(12) United States Patent
Pedrazzini

(10) Patent No.: US 12,221,298 B2
(45) Date of Patent: Feb. 11, 2025

(54) AUTOMATED STATION FOR A PNEUMATIC TRANSPORT SYSTEM FOR HISTOLOGICAL SAMPLES, CONFIGURED FOR THE AUTOMATED LOADING AND/OR UNLOADING OF HISTOLOGICAL SAMPLES, AND PROCESS FOR TRANSPORTING AND HANDLING HISTOLOGICAL SAMPLES

(71) Applicant: Inpeco SA, Novazzano (CH)

(72) Inventor: Gianandrea Pedrazzini, Paradiso (CH)

(73) Assignee: Inpeco SA, Novazzano (CH)

( * ) Notice: Subject to any disclaimer, the term of this patent is extended or adjusted under 35 U.S.C. 154(b) by 217 days.

(21) Appl. No.: 17/944,505

(22) Filed: Sep. 14, 2022

(65) Prior Publication Data

US 2023/0083333 A1 Mar. 16, 2023

(30) Foreign Application Priority Data

Sep. 15, 2021 (IT) .................. 102021000023804

(51) Int. Cl.
  *B65G 51/32* (2006.01)
  *B65G 51/16* (2006.01)
  *B65G 51/36* (2006.01)
  *A61B 10/00* (2006.01)

(52) U.S. Cl.
  CPC ............ *B65G 51/32* (2013.01); *B65G 51/16* (2013.01); *B65G 51/36* (2013.01); *A61B 10/0096* (2013.01); *B65G 2203/0283* (2013.01)

(58) Field of Classification Search
  None
  See application file for complete search history.

(56) References Cited

U.S. PATENT DOCUMENTS 4,465,410 A 8/1984 Vogel et al.
6,146,057 A * 11/2000 Gromley ............... B65G 51/34
                                                406/10

FOREIGN PATENT DOCUMENTS

CN 109160286 A 1/2019

OTHER PUBLICATIONS

Search Report dated Mar. 30, 2022. 2 pages.

* cited by examiner

*Primary Examiner* — William R Harp
(74) *Attorney, Agent, or Firm* — RMCK Law Group PLC

(57) ABSTRACT

A pneumatic transport system for histological samples includes a transport tube within which a carrier containing samples is transported. A station for loading/unloading the samples into/from the carrier is arranged at one tube end. When the carrier is arriving at the station, a blower of the system is deactivated and the carrier is braked, allowing stopping within the station against a stop member. Thereafter, a motor imparts, via the stop member, rotation to said carrier until a carrier door is at an angular position substantially corresponding to an angular position of a station door. Thereafter, the carrier is stopped and the doors are opened by an actuator, this enabling activation of an operating cycle of loading/unloading of the samples. Upon completion, the doors are closed, a carrier locking device is deactivated and the blower is activated, allowing departure of the carrier from the station and its transport within the tube.

20 Claims, 14 Drawing Sheets

AUTOMATED STATION FOR A PNEUMATIC TRANSPORT SYSTEM FOR HISTOLOGICAL SAMPLES, CONFIGURED FOR THE AUTOMATED LOADING AND/OR UNLOADING OF HISTOLOGICAL SAMPLES, AND PROCESS FOR TRANSPORTING AND HANDLING HISTOLOGICAL SAMPLES

CROSS-REFERENCE TO RELATED APPLICATION

This application claims priority to Italian Patent Application No. 102021000023804 filed Sep. 15, 2021. The disclosure of the above application is incorporated herein by reference in its entirety.

FIELD OF THE INVENTION

The present invention relates to pneumatic transport systems for histological samples in anatomical pathology laboratories.

A transport system of this type has already been proposed by the same Applicant in the Italian patent application IT 10 2021 000 009 788, filed on 19 Apr. 2021 and still secret at the priority date of the present invention.

The invention relates in particular to an automated station which can be used in a pneumatic transport system for histological samples able to allow the automated loading and/or unloading of histological samples.

In the present description, and in the following claims, the term "histological samples" is used to indicate any type of organic tissue intended to be treated and handled in an anatomical pathology laboratory. In this context, histological samples are likely to be handled at any step of the treatment process to which they are subjected. For example, histological samples can be transported within containers called "cassettes" before undergoing an embedding operation in a block of embedding material (typically paraffin), or they can be transported after their embedding in a paraffin block, together with the cassettes, in order to be sent towards a cutting operation by means of a microtome, or even, in a step subsequent to the microtome cutting, they can be transported on slides.

The present invention is of a general nature and can be used with any type of histological sample and with any type of holder used to support or contain the histological sample during transport.

The automated station according to the invention can be used, for example, at the input and/or output of any working area or processing apparatus used in an anatomical pathology laboratory, and in particular, for example, at the input and output of an apparatus for embedding an histological sample in a block of embedding material, such as the one that was the object of the Italian patent application IT 10 2021 000 013 757 of the same Applicant, filed on 26 May 2021 and still secret at the priority date of the present invention. As indicated, the invention is in any case of general application.

PRIOR ART

There are, already available on the market, pneumatic transport systems for histological samples, of the type comprising:
  a pneumatic transport tube,
  at least one carrier configured to be pneumatically transported in the pneumatic transport tube and arranged to contain histological samples, and
  a station connected to said pneumatic transport tube, for loading and/or unloading the histological samples.

OBJECT OF THE INVENTION

The object of the present invention is to realize a pneumatic transport system of the type indicated above, which allows to perform a complete automation of the loading and/or unloading operations of the histological samples in/from a station of the transport system.

A further object of the invention is to achieve the aforementioned object with simple and relatively cheap means, but at the same time reliable and safe in operation.

A still further object of the invention is to provide a system which is easily adaptable to any specific application, whatever the type of histological samples to be transported and the type of support on which, or within which, the histological samples are transported.

A further object of the invention is to provide a system in which the entire cycle of operations including the arrival of a carrier carrying the histological samples within a station of the system, the unloading of the histological samples from the carrier and eventually the loading of new samples within the carrier, and the restart of the carrier from the station, can be performed not only in a fully automated way, but also in an extremely short time, to the benefit of laboratory productivity.

SUMMARY OF THE INVENTION

These and further objects of the invention are achieved with a pneumatic transport system for histological samples, comprising:
  a pneumatic transport tube,
  at least one carrier configured to be pneumatically transported in the pneumatic transport tube and arranged to contain histological samples, and
  a station connected to said pneumatic transport tube, for loading and/or unloading the histological samples,
  said system being characterized in that:
  said carrier is in the form of a substantially cylindrical capsule, having a side door with a hinge axis parallel to the axis of the carrier, which side door can be moved between a closed position, for the transport of the histological samples through the pneumatic transport tube, and an open position, for the loading and/or unloading of the histological samples in/from the station,
  said station comprises a station tubular structure coaxially connected to said pneumatic transport tube and arranged to receive the carrier at the end of a stroke of the carrier within the pneumatic transport tube, said station tubular structure having a door in a side wall thereof, with a hinge axis parallel to the axis of the pneumatic transport tube, which door can be moved between a closed position and an open position,
  said station further comprises a stop member, to stop said carrier when the carrier reaches a final position within the station, and a servo-controlled electric motor, to impart a rotation to said carrier around its axis, by means of said stop member, until a mating condition is reached in which the side door of the carrier is at an angular position substantially corresponding to the angular position of the door of the station tubular structure, said station further comprises an actuator to control a rotation of the door of the station tubular structure between its closed position and its open position, said door of the station tubular structure and said door of the carrier are configured so as to engage each other when the door of the carrier is in said mating condition and the aforementioned actuator controls an opening of the door of the station tubular structure, so that an opening of the door of the station tubular structure also causes an opening of the door of the carrier, said system comprising an electronic controller configured to:

activate said servo-controlled electric motor which controls the rotation of the carrier about its axis after the electronic controller has received a signal from a sensor which detects the arrival of the carrier at its final position in the station, stop said servo-controlled electric motor, so as to stop the aforementioned rotation of the carrier about its axis and activate said actuator which controls the opening of the door of the carrier and of the door of the station, when the electronic controller receives a signal from a sensor which detects that the aforementioned mating condition of the door of the carrier and the door of the station has been reached, so that when said carrier reaches said station, accessibility to the histological samples contained in the carrier is obtained in an automated manner.

In the preferred embodiment, the system comprises a manipulator robot for the automatic loading and/or unloading of histological samples into/from the carrier, said electronic controller being configured to enable a cycle of operations of said manipulator robot after the electronic controller has received a signal from the aforementioned sensor which detects the aforementioned mating condition of the door of the carrier and of the door of the station, and/or a signal from a sensor which detects the open condition of the door of the station and/or the open condition of the door of the carrier.

According to a further preferred feature, said station tubular structure is provided with an electrically operated locking device, to lock the carrier in said mating condition of said door of the carrier and said door of the station and in that said electronic controller is configured to activate said locking device after the electronic controller has stopped the aforementioned rotation of the carrier and before the electronic controller controls the opening of the door of the station and the door of the carrier.

When a carrier is arriving at the station, the movement of the carrier must be slowed down. For this purpose, a sensor located in a position spaced apart from said station, and configured to detect the passage of a carrier arriving at the station, is associated with said pneumatic transport tube. The electronic controller is configured to deactivate a blower of the pneumatic transport system when the electronic controller receives from said sensor a signal indicating the passage of a carrier arriving at the station. Furthermore, preferably, the pneumatic transport tube is provided, adjacent to said station tubular structure, with a braking device to brake the movement of the carrier and comprising one or more elastically biased flaps, protruding inside the pneumatic transport tube and configured so that the flaps engage the carrier when the carrier is close to reaching the station, so as to slow the carrier down, while the flaps do not substantially oppose the movement of the carrier when the carrier leaves again from the station and moves in the opposite direction in the pneumatic transport tube.

In the aforementioned preferred embodiment, the stop member able to impart a rotation to the carrier about the axis of the carrier is rotatably mounted at one end of said station tubular structure and is provided with shock-absorbing pads configured to be engaged by a front wall of the carrier when it reaches its final position within the station at the end of a stroke in the pneumatic transport tube.

Still in the case of the aforementioned preferred embodiment, the station is provided with sensors to detect a closed condition of the door of the station and/or of the door of the carrier and to detect an open condition of the door of the station and/or of the door of the carrier.

In one example, the door of the carrier is biased towards the open position by one or more springs and is instead normally held in its closed condition by magnetic engagement members provided on the wall of the carrier and on the door of the carrier. Still in the case of the preferred embodiment, the door of the station is provided with an electrically operated lock for locking the door of the station in its closed condition.

Still in the preferred embodiment, the pneumatic transport tube, preferably of substantially transparent material, comprises an end portion inserted within said station tubular structure through the entire axial extension of said station tubular structure. The end portion of the pneumatic transport tube has a window at the door of the station. Thanks to this feature, the connection between the station tubular structure and the pneumatic transport tube is free from the risk that in the final step of approach of a carrier in the station, pressure variations which tend to hinder the movement of the carrier can occur.

The carrier used in the system according to the invention can be easily equipped with a structure configured according to the type of supports or containers of histological samples to be transported, in order to ensure that said supports and/or containers remain in a stable position during transport.

The invention also relates to the process for transporting and handling histological samples carried out by means of the system described above.

As it is evident from the above, in the case of the preferred embodiment, when a carrier moving in the pneumatic transport tube reaches the station, its presence is detected and the transport system blower is deactivated, by means of the electronic controller, after which the movement of the carrier is further slowed down by means of the aforementioned elastically biased flaps. The impact of the carrier against the stop member in the station is damped by the aforementioned shock-absorbing pads. The presence of the carrier within the station is detected by the aforementioned sensor, which activates, again by the electronic controller, the servo-controlled electric motor which puts in rotation the carrier about its axis until a corresponding sensor detects the reaching of the mating condition of the door of the carrier with the door of the station. When this condition is reached, it is activated, by means of the electronic controller, the electrically operated locking device which locks the carrier in this position, which also determines the activation of the actuator which controls the opening of the door of the station. In its opening movement, the door of the station engages the door of the carrier which is then forced to open, against the action of the magnetic effect members tending to keep it closed. The movement of the door of the carrier towards the open position is helped by the aforementioned springs which are associated with the door. When the reaching of the open condition of the door of the station and the door of the carrier is detected by the corresponding sensor, it is activated, by the electronic controller, the cycle of operations of the manipulator robot, which picks up the supports containing the histological samples (e.g. sample-holding cassettes) from within the carrier. Once the working cycle of the manipulator robot is finished, the door of the station is closed, again by means of the electronic controller, causing a corresponding closure of the door of the carrier and the electric lock for locking the door of the station in the closed condition is activated. Once this condition is reached, the electronic controller deactivates the locking device that kept the carrier in the locked position and activates the blower of the pneumatic transport system in order to bring the carrier out from the station, making it travel in the pneumatic transport tube.

In the present description, and in the following claims, the term "electronic controller" is used to include both the case of a single electronic unit configured to perform the described operations, and the case of several electronic units separated from each other and configured to perform each a part of the operations described herein.

In a particularly preferred embodiment, the pneumatic transport tube and the station tubular structure are oriented with their axis directed vertically, and with the station tubular structure associated to a lower end of the pneumatic transport tube. In any case, it is possible to provide for different orientations of the system.

In a typical application, the above-described station is provided at each of the two opposite ends of a pneumatic transport tube, and a single carrier travels along the tube between the two stations. However, different applications can be provided, for example with multiple transport lines in parallel and it is not even excluded the use of a station of the described type as an intermediate station, between two end stations of the transport line.

BRIEF DESCRIPTION OF THE DRAWINGS

Further features and advantages of the invention will emerge from the following description with reference to the attached drawings, provided purely by way of non-limiting example, wherein.

DETAILED DESCRIPTION OF A PREFERRED EMBODIMENT

Figure 1:
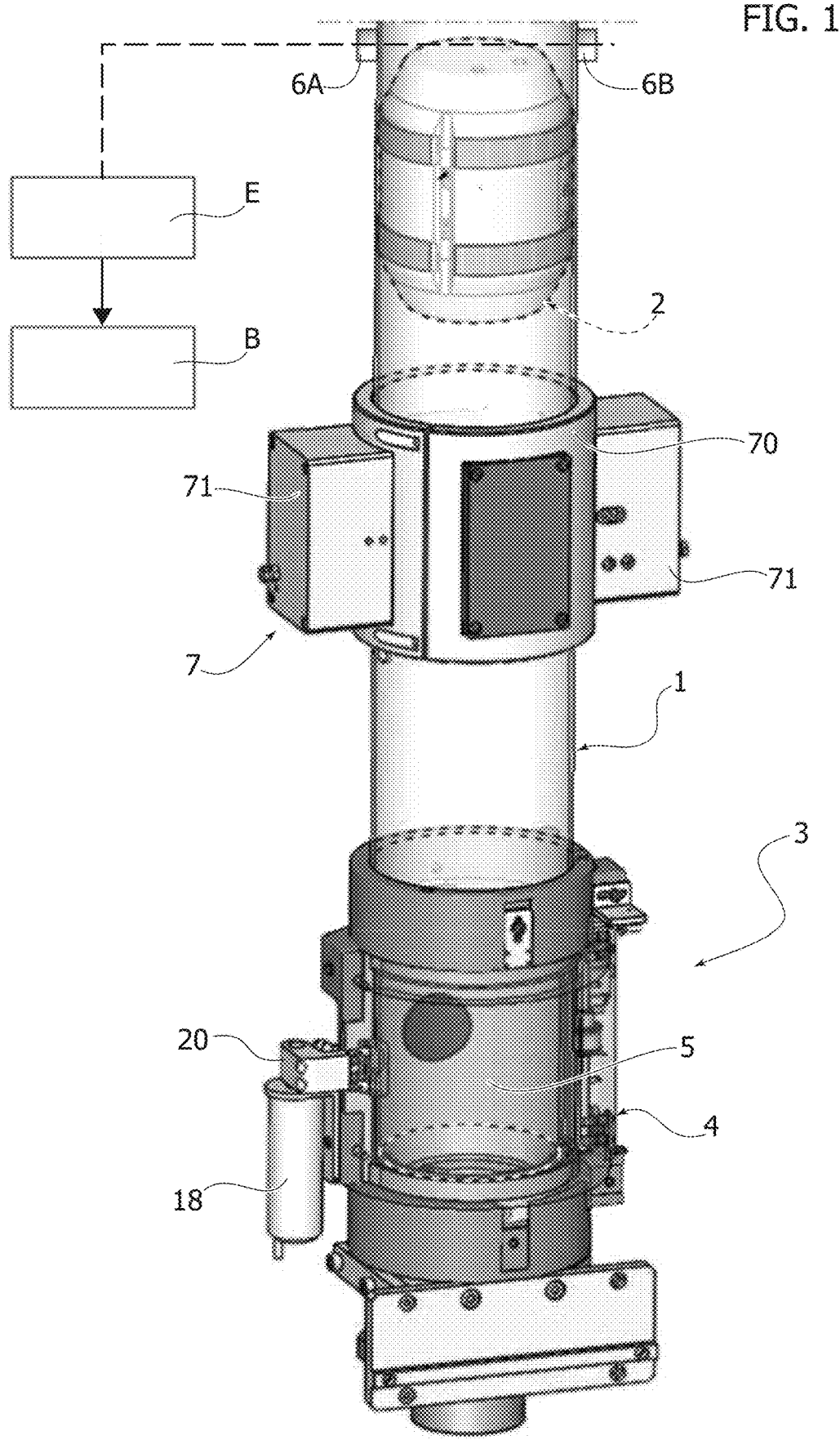
FIG. 1 is a perspective view of a pneumatic transport system according to the invention, with an automated station for loading and/or unloading histological samples.

In the drawings, reference 1 indicates as a whole a pneumatic transport tube of a pneumatic transport system for histological samples according to the present invention.

Pneumatic transport systems have been known for some time. In general, they provide a pneumatic transport tube and one or more blowers suitable for generating a flow of pressurized air within the pneumatic transport tube, in order to cause the movement of one or more carriers within the pneumatic transport tube, in one direction or another.

In the present description, and in the attached drawings, the construction details related to the arrangement of the blowers of the pneumatic transport system and to the control means of the blowers are neither described nor illustrated, as they can be made in any known way and do not fall, taken on their own, within the scope of the present invention.

The attached drawings show a preferred embodiment of a pneumatic transport system according to the invention, with an automated station for loading and/or unloading the histological samples.

Figure 4:
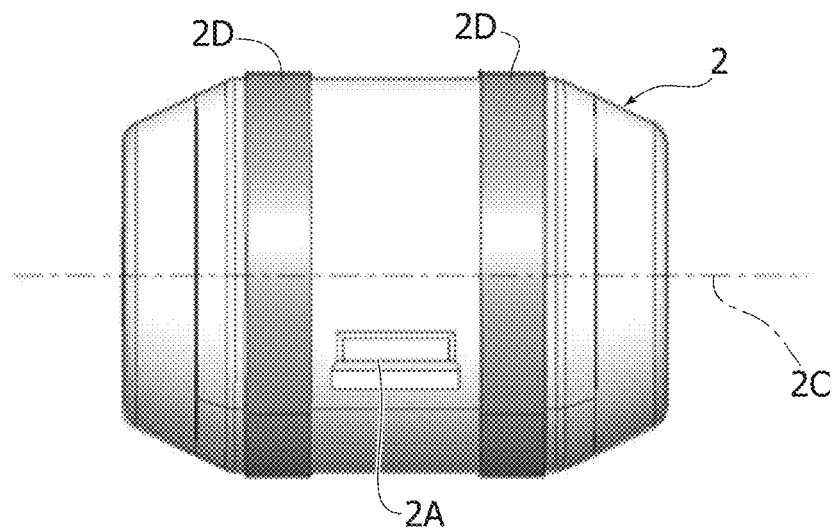
FIG. 4 is a side view of a carrier used in the system according to the invention.

In the drawings, number 1 indicates as a whole a pneumatic transport tube of the system according to the invention. With reference in particular to FIGS. 1 and 4, the system is arranged with a carrier 2, intended to transport histological samples, and configured to travel within the pneumatic transport tube 1.

In the illustrated embodiment, the carrier 2 provided in the system according to the invention is in the form of a cylindrical capsule (which in the example has conical opposite ends) having a maximum external diameter slightly lower than the internal diameter of the pneumatic transport tube 1.

In the specific example illustrated, on the external side surface of the cylindrical carrier 2 there are two rings 2D of a synthetic material with a low friction coefficient, intended to facilitate the sliding of the carrier 2 within the pneumatic transport tube 1.

Still with reference to FIG. 1, number 3 indicates as a whole a station of the pneumatic transport system, comprising a station tubular structure 4 coaxially connected to the end portion of the pneumatic transport tube 1.

The example illustrated herein provides for a vertical orientation of the end portion of the pneumatic transport tube 1 and of the station tubular structure 4, with the tubular structure 4 arranged at the lower end of the tube 1, but the invention is also applicable with any different orientation of the tube 1 and the structure 4.

Again, in the preferred embodiment, it can be provided that an end station identical to the one illustrated herein is arranged at the opposite end of the pneumatic transport tube 1, and that a single carrier 2 travels in one direction or the other, from one station to the other. However, different applications can be provided, for example with multiple transport lines in parallel and it is not even excluded the use of a station of the described type as an intermediate station, between two end stations of the transport line.

Preferably, the pneumatic transport tube 1 is of transparent synthetic material.

Figure 2:
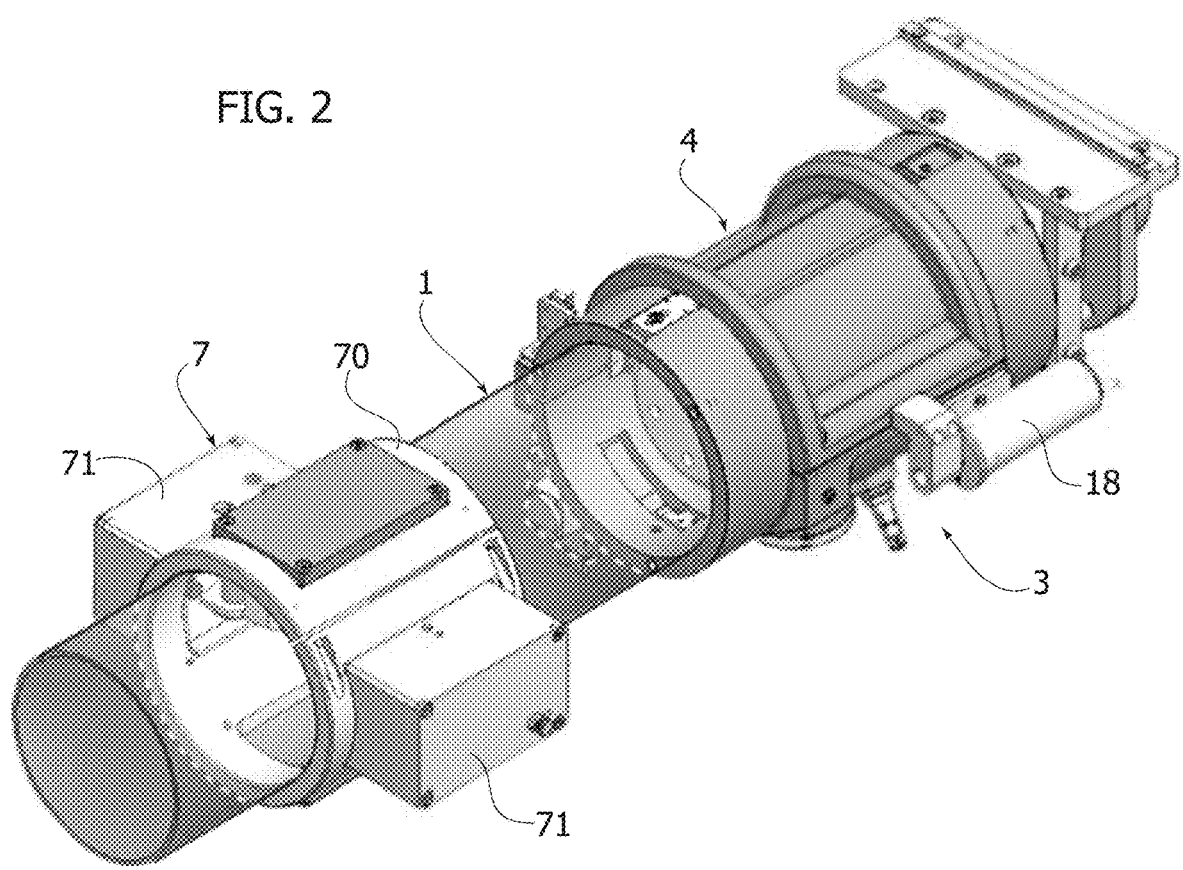
FIG. 2 is a further perspective view of the station of FIG. 1.
Figure 3:
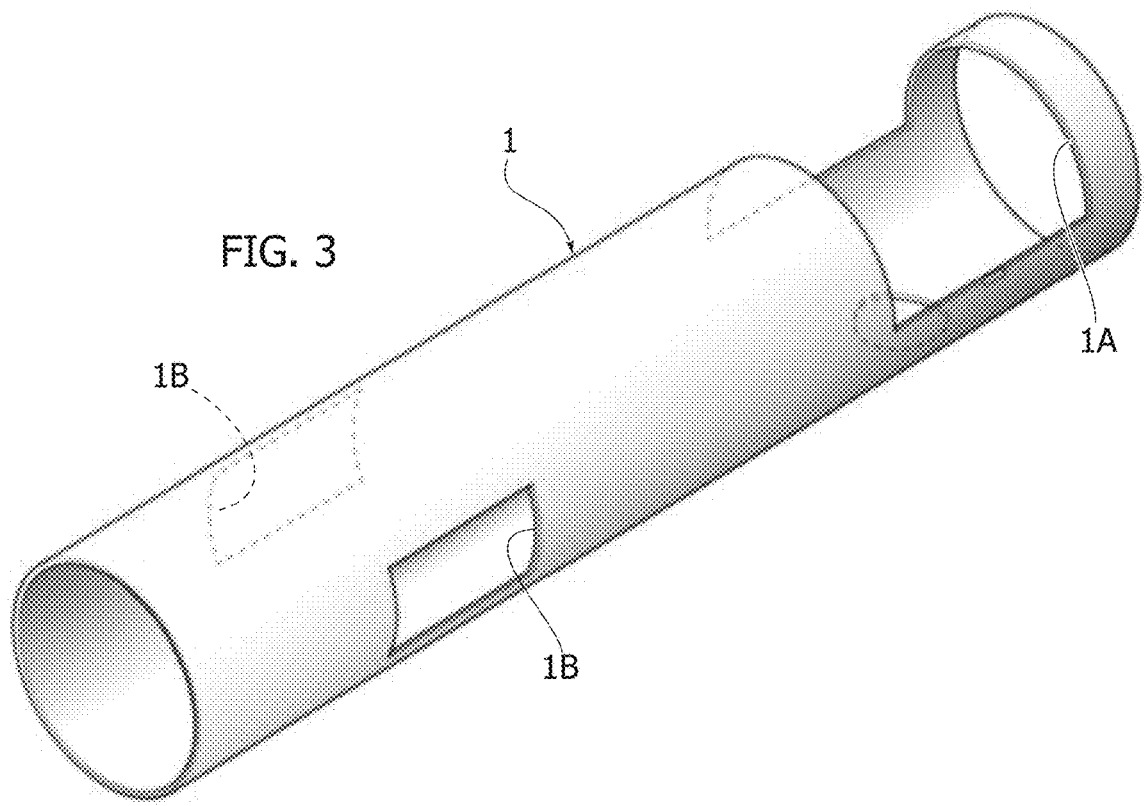
FIG. 3 is a perspective view of an end portion of a pneumatic transport tube associated with the station according to the invention.

With reference also to FIGS. 2, 3, the end portion of the pneumatic transport tube 1 is preferably inserted within the tubular structure 4 of the station 3 for the entire axial extension of the tubular structure 4. Thanks to this feature, the connection between the station tubular structure and the pneumatic transport tube is free from the risk that in the final step of approach of a carrier in the station pressure variations within the tube which tend to hinder the movement of the carrier can occur.

However, if this is not possible, in order to anyway provide a full adaptability of the system i.e. to ensure in any case an appropriate interfacing with the end portion of the pneumatic transport tube 1, the station 3 can be provided, at the end facing the tube 1, with a bushing with a telescopic gasket (not shown in the figures) which allows the pneumatic transport tube 1 to slide inside it along its axis, coinciding with the axis of the station, so as to ensure a certain displacement, preferably up to about 100 mm.

Figure 12:
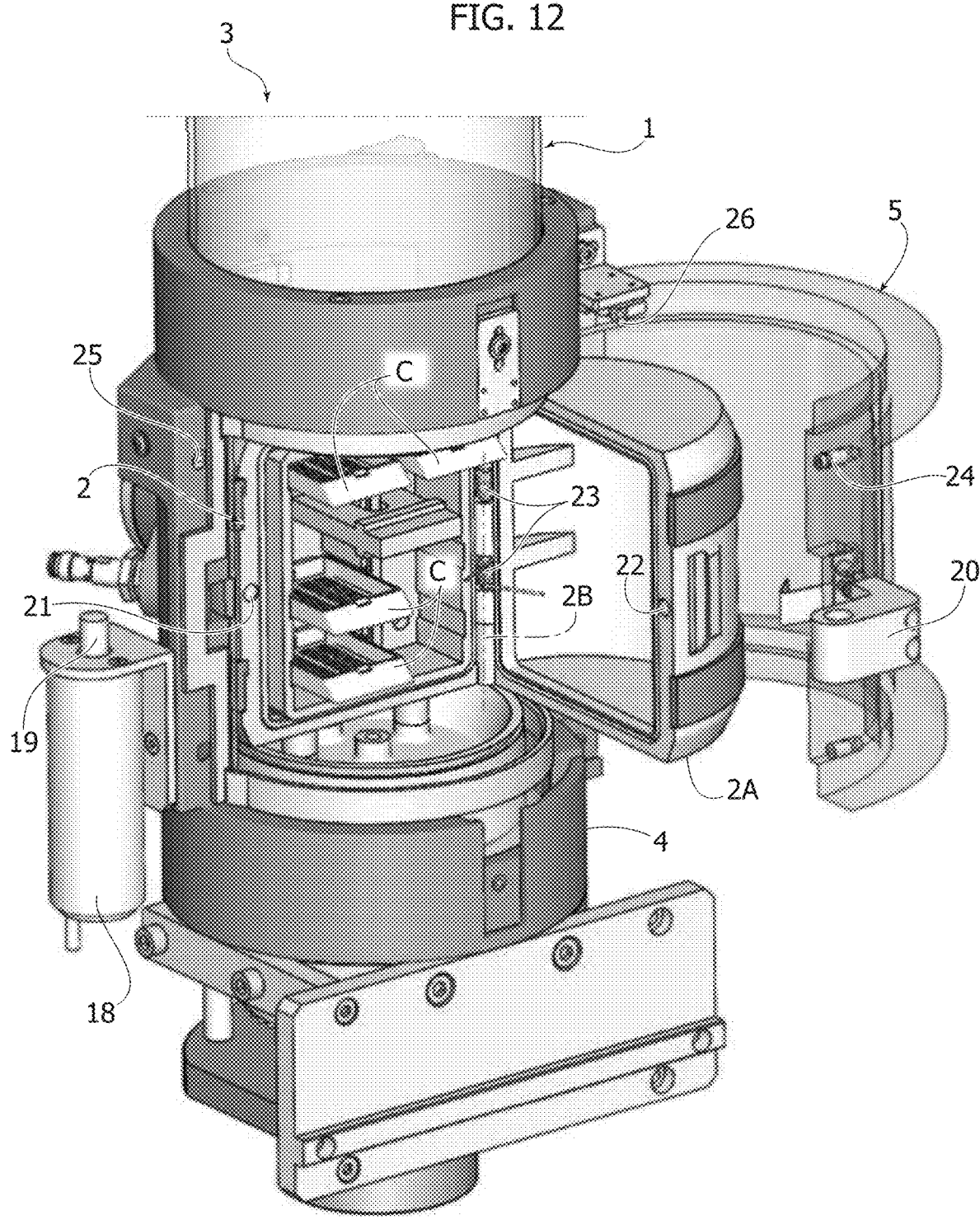
FIG. 12 is a perspective view showing the carrier in the station, with the carrier door and the station door both open.

With reference to FIGS. 1 and 12, the wall of the tubular structure 4 of the station 3 includes a side door 5 with a hinge having an axis 4A (see FIG. 10A) parallel to the common axis 12 of the tubular structure 4 and of the tube 1 and which is movable between a closed condition (illustrated in FIG. 1) and an open condition (illustrated in FIG. 12). With reference to FIG. 12, even the carrier 2 has a portion of its body constituting a side door 2A hinged to the remaining part of the carrier body about an axis 2B parallel to the axis 2C (FIG. 4) of the carrier 2.

As described in detail below, when a carrier 2 arrives in station 3, it is oriented in such a way as to make the door 2A of the carrier 2 and the door 5 of the station tubular structure 4 mate in position, in order to then be able to open both doors 5, 2A and access within the carrier.

In a practical embodiment, the end portion 1 of the pneumatic transport tube has an external diameter of 100 mm and a wall thickness of 2 mm, so as to have an internal diameter of 96 mm.

Still with reference to FIG. 1, in the preferred embodiment an optical sensor, able to detect the passage of the carrier 2 arriving the station, is associated to the end portion of the pneumatic transport tube 1, in a sufficiently spaced position with respect to the station 3. In the example, the optical sensor comprises an emitter 6A and a receiver 6B of any known type, able to detect when the optical line between the emitter and the receiver is interrupted and then restored after the passage of the carrier 2.

According to the invention, the optical sensor 6A, 6B sends a signal indicative of the passage of a carrier 2 arriving at the station to an electronic controller E which consequently deactivates a blower B (shown only schematically in FIG. 1) intended to create the flow of pressurized air within the pneumatic transport tube 1.

In this way, when the carrier 2 intercepts the optical sensor 6A, 6B, the blower B is deactivated and the carrier continues its movement solely by inertia.

Again with reference to FIG. 1, downstream of the sensor 6A, 6B (with reference to the direction of movement of the carrier 2 towards the station 3) there is a braking system 7 which causes a further slowing down of the carrier 2 arriving at the station.

Figure 5A:
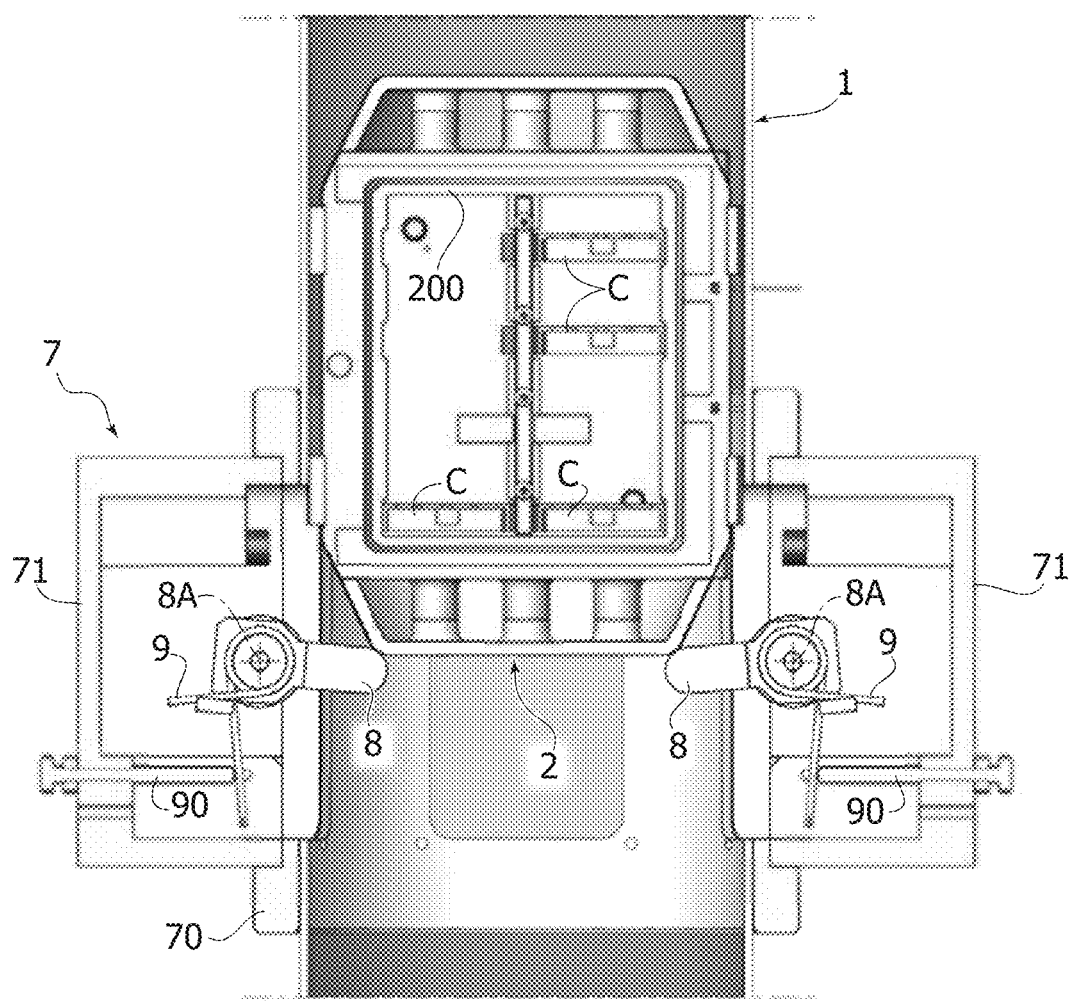
FIGS. 5A, 5B are sectional views of the pneumatic transport tube, in a plane containing the axis of the tube, which illustrate two successive positions of the carrier in a step of its movement towards the station (downwards, with reference to the drawing)
Figure 5B:
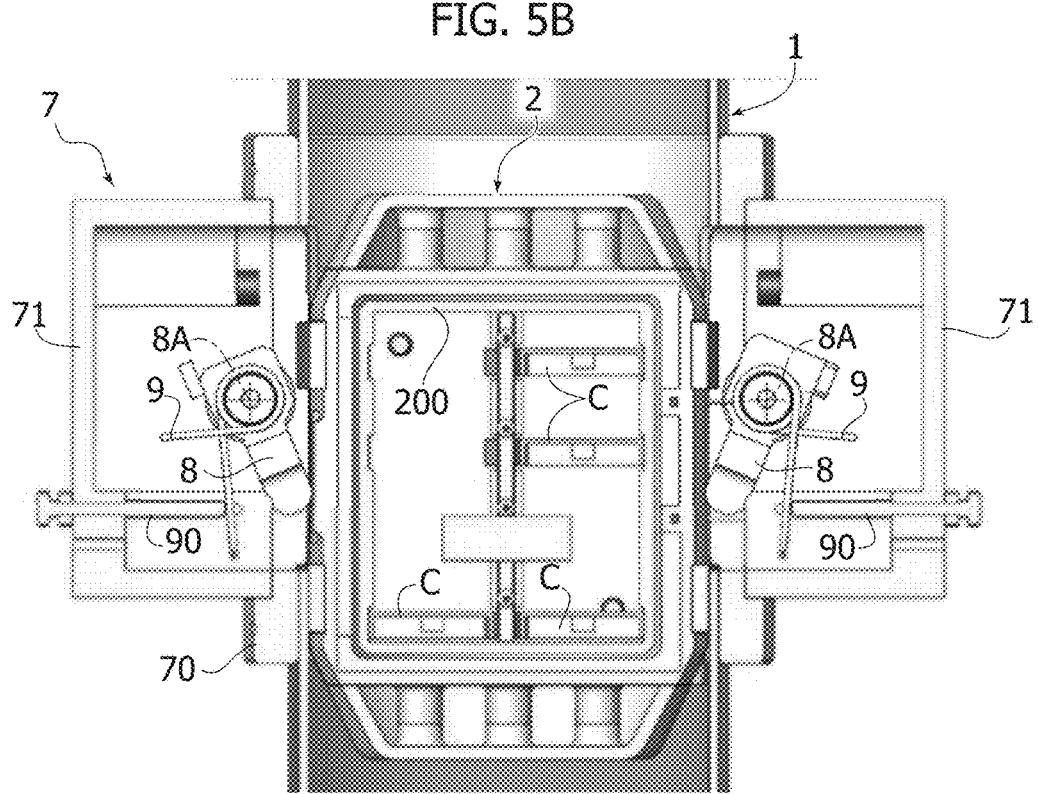
Figure 6:
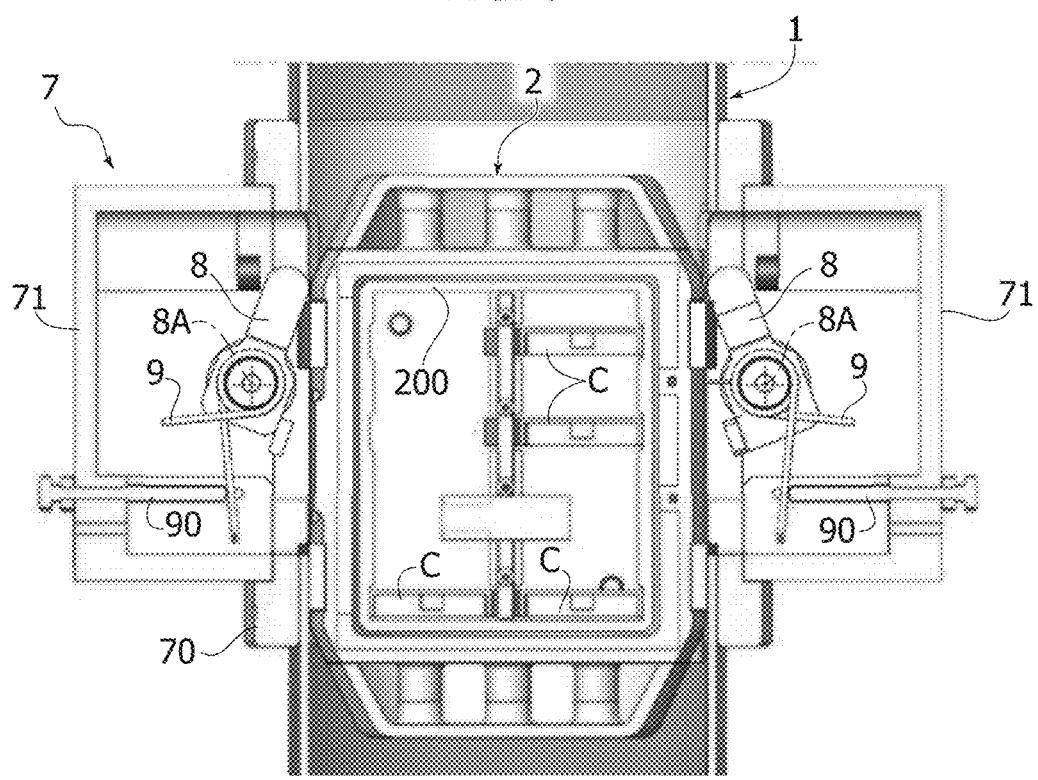
FIG. 6 is a sectional view similar to those of FIGS. 5A, 5B showing the carrier during a subsequent step in which it has left the station and is moving away from the station (upwards, with reference to the drawing)

With reference to FIGS. 5A, 5B and 6, the braking system 7 comprises a tubular support 70 surrounding the tube 1 which carries a pair of casings 71 containing flaps 8 which protrude inside the end portion of the pneumatic transport tube 1 (through windows 1B of the tube 1, visible in FIG. 3). The flaps 8 are rotatably mounted about axes 8A in the casings 71 and are each recalled by a respective spring 9. In the illustrated example, each spring 9 is a wrapped spring, having one end operatively connected to the body of the respective flap 8 and the opposite end able to come into contact with an abutment member constituted by a screw 90 mounted in the casing 71. The arrangement is such that when a carrier 2 is approaching the station (i.e. it is moving downwards, with reference to the drawings) it meets the flaps 8, which consequently rotate in the direction in which they tension the springs 9, due to the engagement of the springs 9 against the screws 90. In this step, therefore, the flaps 8 tend to hinder the movement of the carrier 2, due to the return of the springs 9, so as to brake its movement. FIG. 5A shows an initial step of the engagement of the flaps 8 against the lower end of the carrier, while FIG. 5B shows a subsequent step, in which the carrier has moved further downwards and the flaps 8 are in sliding contact with the side wall of the carrier, which therefore continues to be braked by friction. On the contrary, when a carrier 2 leaves the station and moves away from it within the pneumatic transport tube 1 (see FIG. 6), i.e. moving upwards with reference to the drawings, the flaps 8 rotate in the direction that does not cause a tensioning of the springs 9, so that the flaps 8 substantially do not oppose such movement of the carrier 2.

Returning again to FIG. 1, once the carrier 2 has been slowed down in its movement towards the station 3, it finally reaches its end position within the station tubular structure 4.

The arrival of a carrier 2 in the end position within the station tubular structure 4 is detected by an optical sensor (not shown) totally similar to the detection system 6A, 6B. In this case the sensor (optical emitter and optical receiver) is associated with the tubular structure 4 of the station 3, in a position such that its optical line is intercepted by the carrier 2 when the latter is close to reaching its end position within the station (downwards with reference to the drawings) or is already in this end position. Even in this case, the sensor is connected to the electronic controller of the system.

Figure 7:
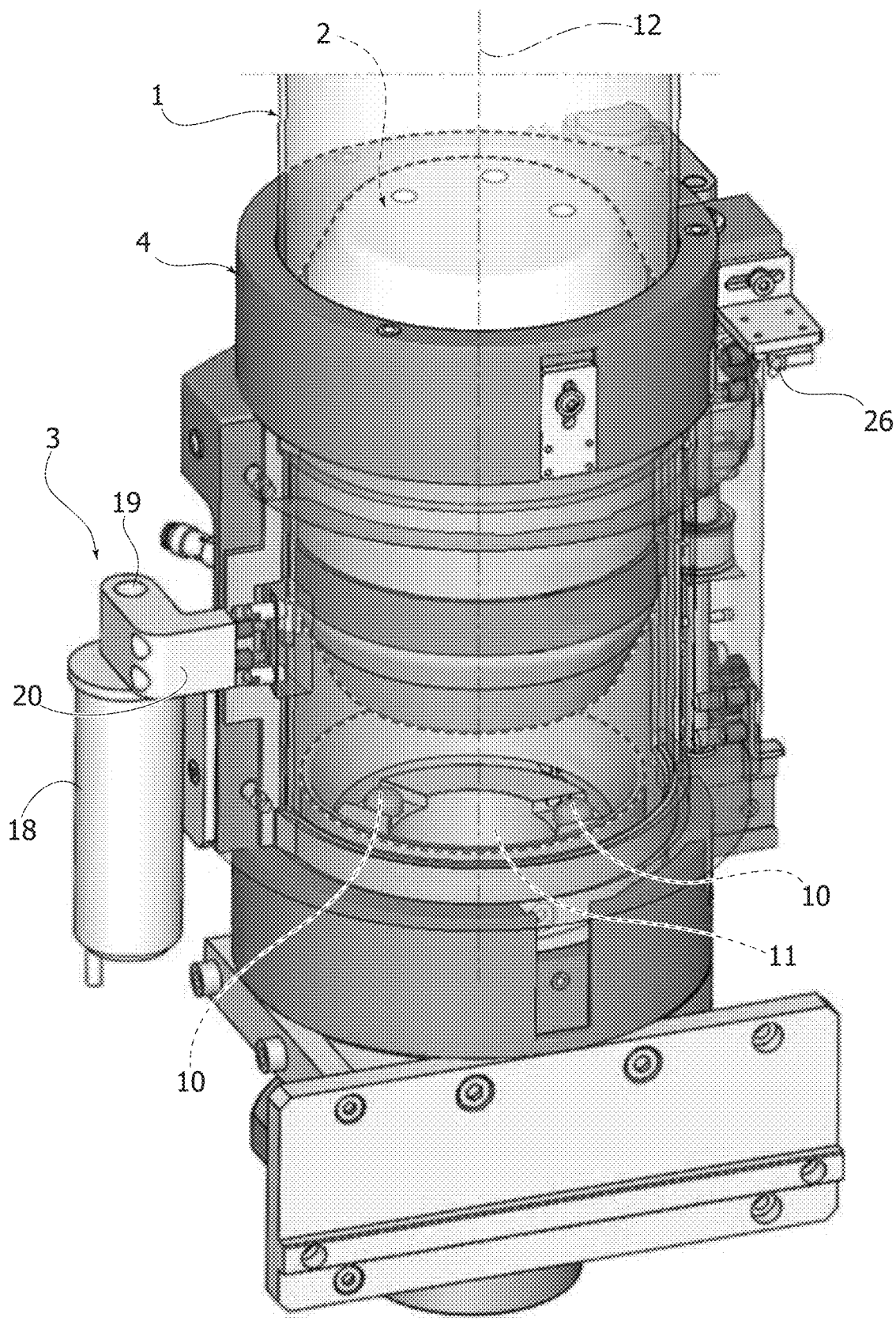
FIG. 7 is a further perspective and enlarged scale view of the station according to the invention.
Figure 7A:
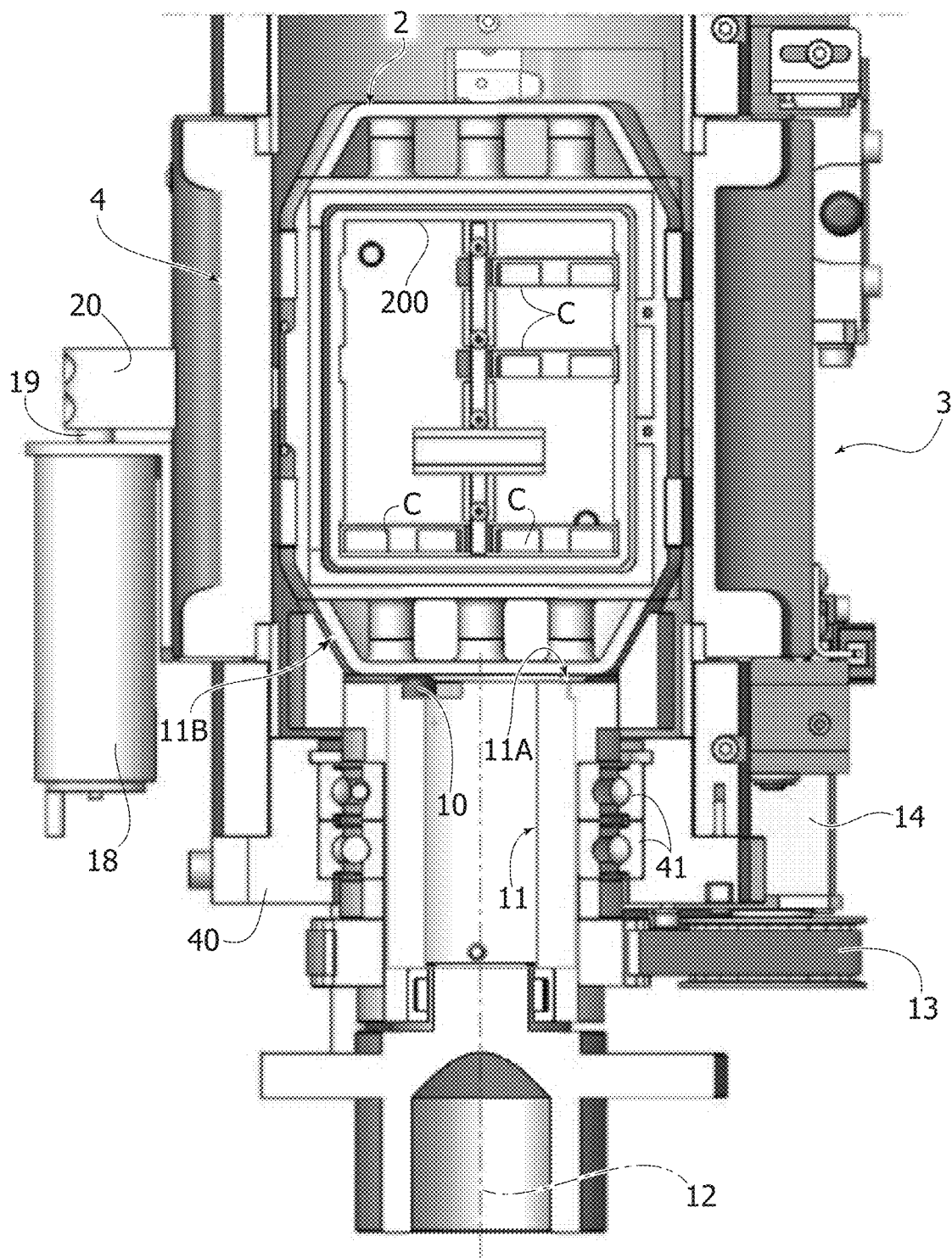
FIG. 7A is a sectional view of the station in a vertical plane.
Figure 8:
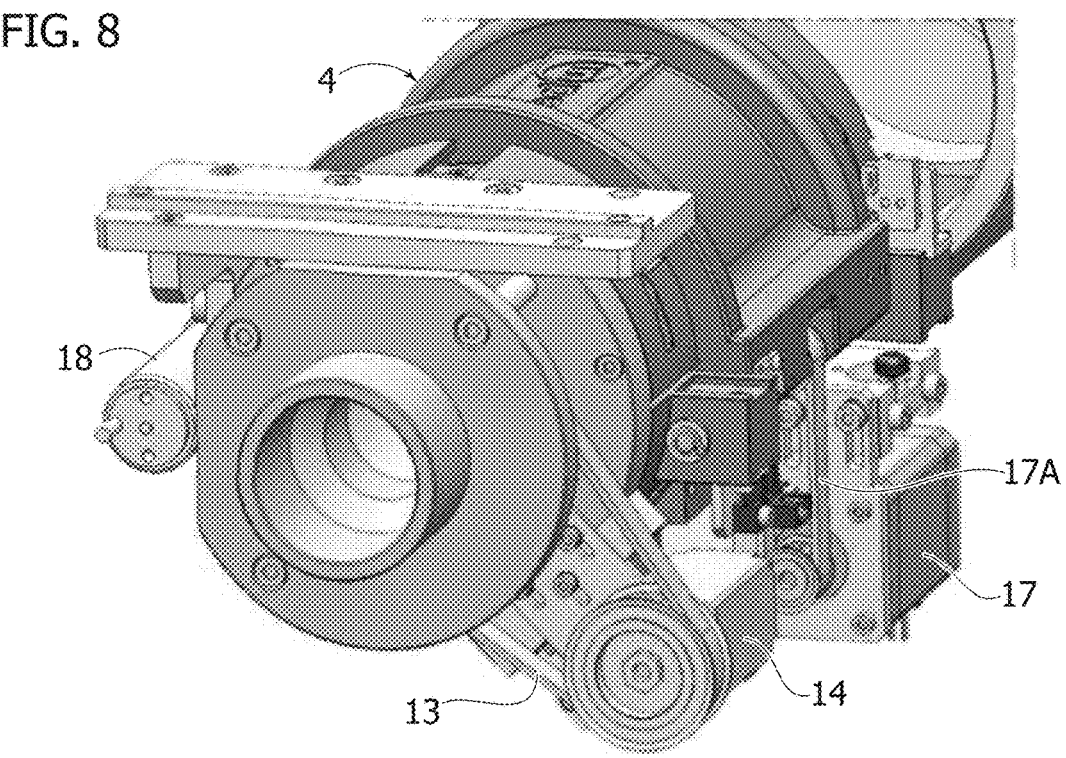
FIG. 8 is a further perspective view from one end of the station.

With reference in particular to FIGS. 7, 7A and 8, on the lower end of the tubular structure 4 of the station 3 there is fixed a bushing 40 which supports in rotation, about the axis 12 of the tubular structure 4, a stop member 11, which with its upper end surface just contributes to stop the carrier 2 in the final position of the carrier 2 within the station (illustrated in FIG. 7A).

In the example shown, the upper surface of the stop member 11 has a flared shape, adapted to the conical shape of the end of the carrier intended to be received thereon. In particular, the aforementioned surface has a flat central portion 11A bearing rubber shock-absorbing pads 10, to dampen the impact with the carrier 2. The central flat portion 11A is surrounded by a conical circumferential portion 11B carrying a rubber shock-absorbing coating.

Figure 9:
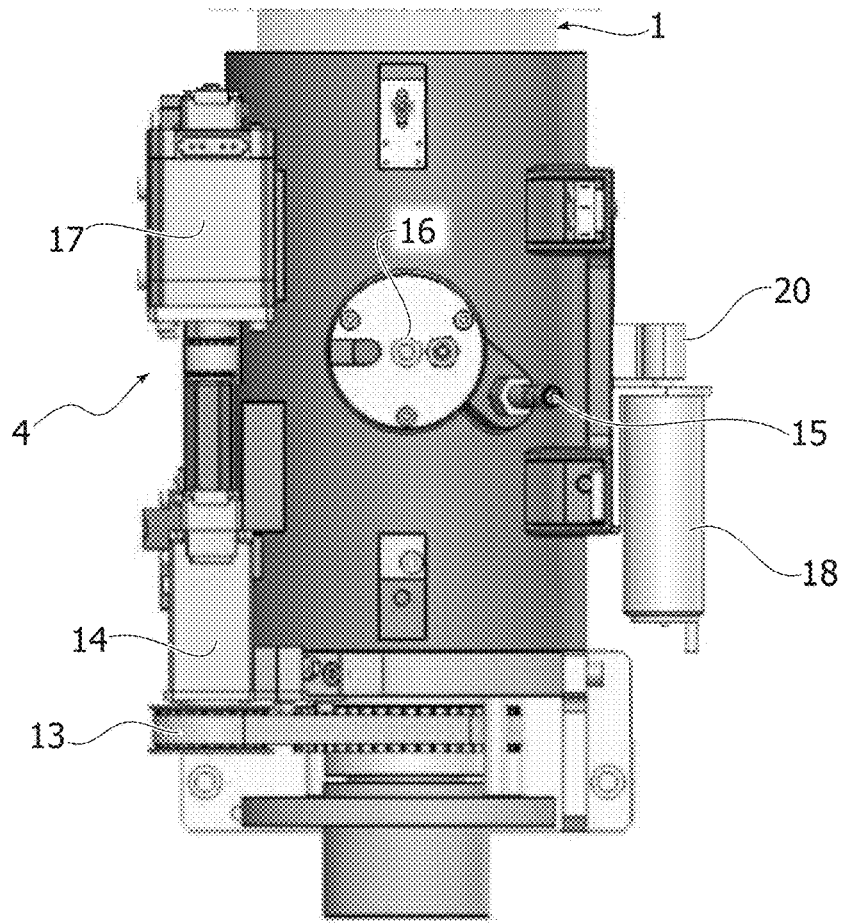
FIGS. 9-10 are a side view and a further perspective view of the station.
Figure 10:
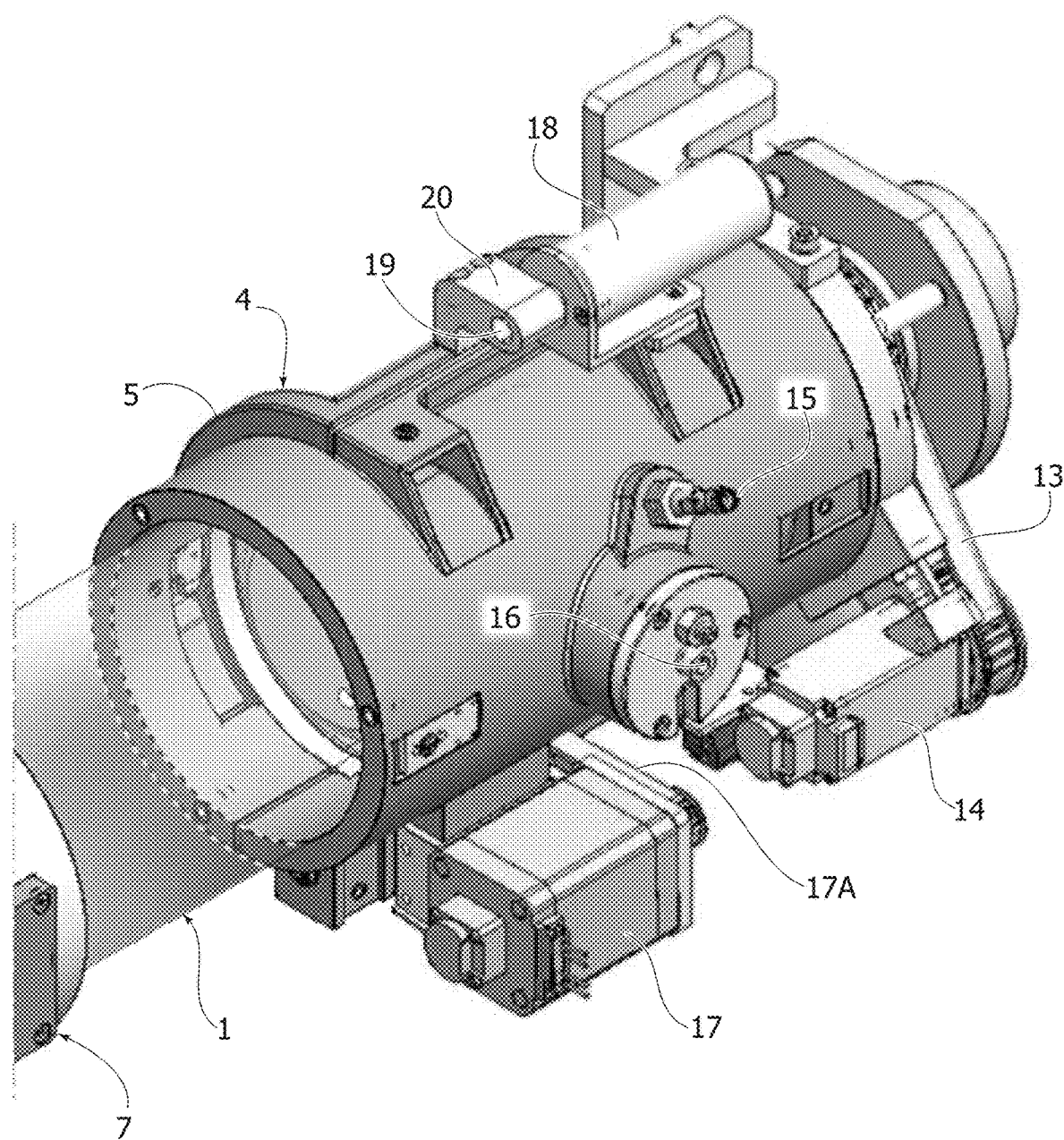
Figure 10A:
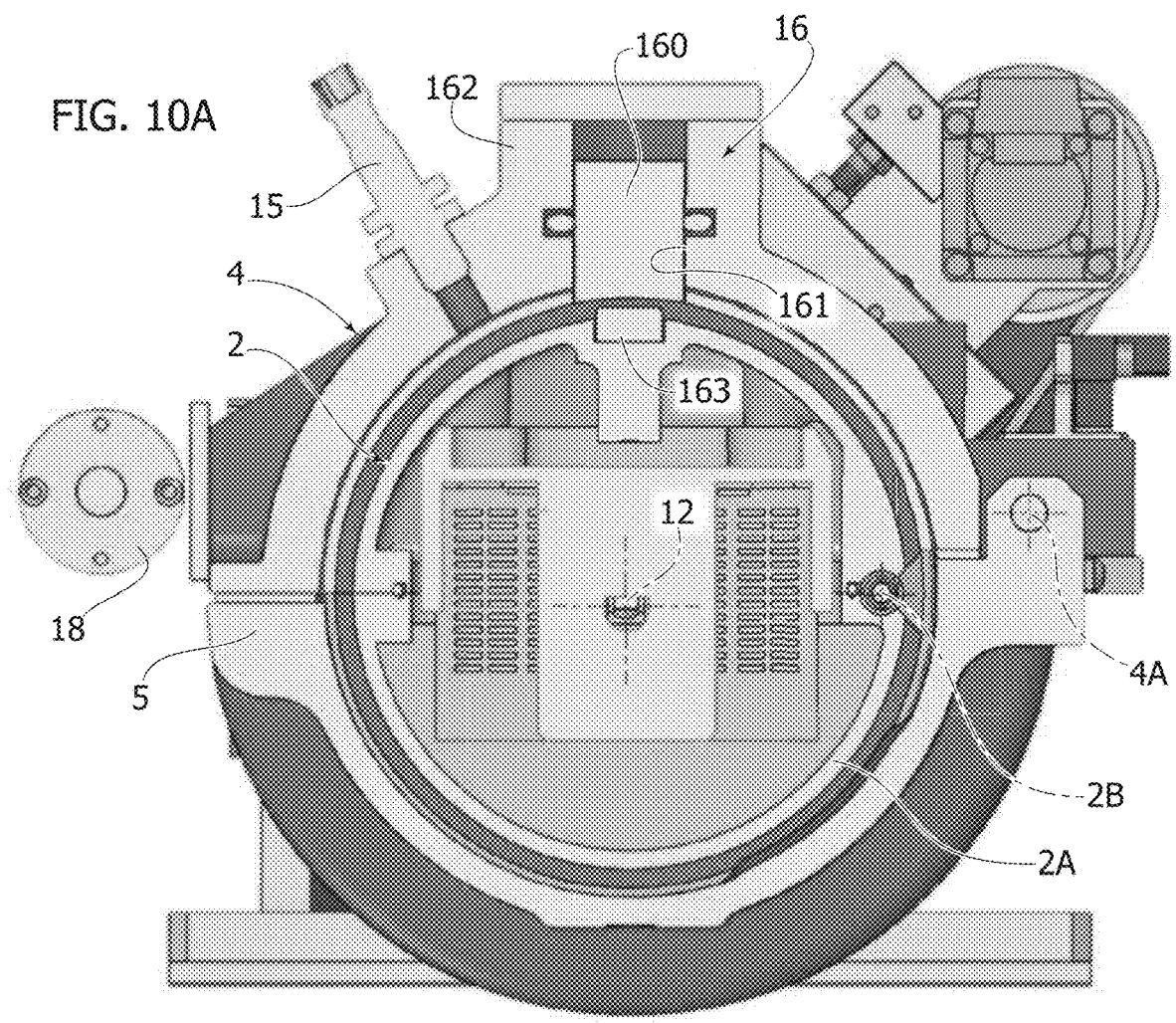
FIG. 10A is a sectional view of the station, in a plane orthogonal to the axis of the station, with a carrier arranged within it.

The stop member 11 can be placed in rotation around the axis 12 of the station, by means of a belt transmission 13, by a servo-controlled electric motor 14 (see also FIGS. 9, 10).

When the arrival of a carrier at the station is signaled by the sensor provided for this purpose, the electronic controller E activates the electric motor 14, which rotates the stop member 11. The rotation of the rotatable stop member 11 causes by friction, thanks to the engagement of the pads 10 and of the rubber-coated portion 11B against the end wall of the carrier 2, a rotation of the carrier 2 around the axis of the carrier, coinciding with the axis 12 of the station.

This rotation is controlled to bring the carrier into a mating condition in which the door 2A of the carrier 2 is in an angular position very close to the angular position of the door 5 of the station, even if not yet perfectly aligned. For this purpose, a sensor 15 (see in particular FIG. 10A) is associated with the station tubular structure 4, which sensor being in the example of the magnetic type and able to detect a key 163 of ferromagnetic material present on the outer surface of the carrier 2, which is in front of the sensor 15 when the carrier 2 is in the angular position close to the mating of the door 2A of the carrier with the door 5 of the station 3.

At this point a reverse rotation of the stop member 11 by a predetermined number of degrees, brings the key 163 into alignment with an electric locking device 16, simultaneously activated by the electronic controller E, which locks the carrier 2 in the reached position, preventing further rotations or axial movements thereof since the condition of substantial correspondence, that is the mating of the doors 2A, 5, has been reached. In the example illustrated in FIG. 10A, the locking device 16 comprises an electromagnet 160 mounted within a recess 161 of a support 162 and able to interact by magnetic effect, when activated, with the key 163 of ferromagnetic material carried by the side wall of the carrier 2, to lock the latter in position.

Once the aforementioned mating condition of the doors 2A, 5 has been reached and once the carrier 2 has been locked in this position, the electronic controller E activates an electric motor 17 (FIG. 10) arranged to control the opening of the side door 5 of the tubular structure 4 of the station by means of a belt 17A, connected to a hinge pivot rotatable with the door (see FIG. 8).

Figure 11:
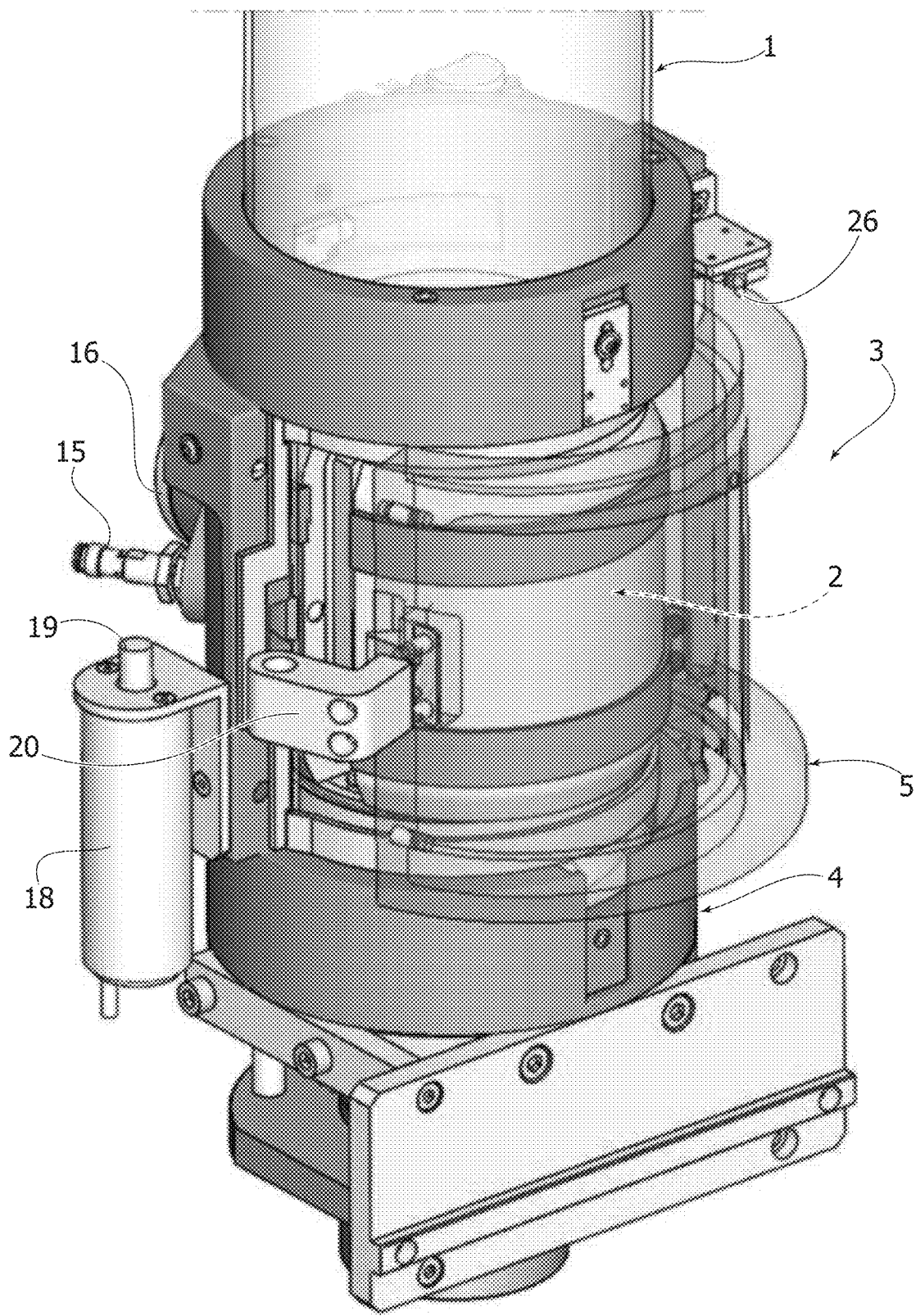
FIG. 11 is a further perspective view of the station.

It should be considered that in the preferred embodiment, when the door 5 is in the closed condition, it is locked in this condition by an electric lock 18 carried by the structure 4 of the station and able to control the axial movement of a bolt 19 able to engage a through hole of a fin 20 of the door 5 (see FIGS. 10, 11 and 12). Therefore, when the carrier is locked in the mating position of the doors 2A, 5, the electric lock 18 is deactivated by the controller E, after which the electric motor 17 is activated, still by the controller E, to control the opening of the door 5 (FIG. 12).

Figure 10B:
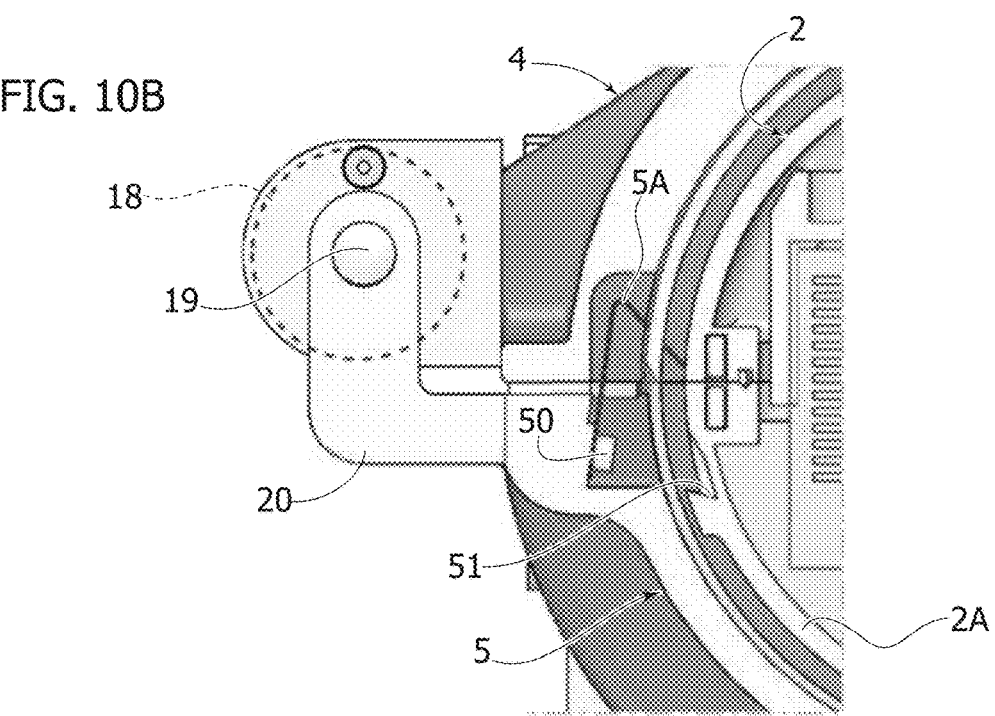
FIG. 10B shows a detail of a section similar to that of FIG. 10A.

With reference again to FIG. 10B, the door 5 of the structure 4 of the station has an elastic flap 5A, having one end anchored by a screw 50 to the body of the door 5, and which has a free portion, substantially shaped like a hook, tending to be elastically recalled towards a position rotated in a clockwise direction (with reference to FIG. 10B). In the closed condition of the door 5, illustrated in FIG. 10B, the flap 5A is then pressed against the outer surface of the carrier 2. When the flap 5 is opened, the flap 5A snaps elastically into a housing 51 of the outer surface of the door 2A of the carrier, so as to hook the door 2A and drag it towards the open position, after the opening of the door 5.

The opening of the door 2A of the carrier 2 is obtained against the action of two magnetic effect engagement members 21, 22 (FIG. 12), respectively associated with the body of the carrier 2 and with its door 2A, and able to come into contact with each other in the closed condition of the door 2A of the carrier 2, so as to tend to keep the door 2A in closed condition. When the door 5 of the station is opened, it causes, through the elastic flap 5A, the opening of the door 2A of the carrier 2, against the magnetic action of the elements 21, 22, after which the opening movement of the door 2A is further favored by springs 23 associated with the joint hinge of the door 2A. When the door 5 is then closed again, it brings the door 2A back towards the closed position simply following the contact of the internal surface of the door 5 with the door 2A, until the two magnetic effect engagement members 21, 22 ensure the perfect closure of the door 2A. As a further refinement of such closure operation a motorized mechanism (not shown in the figures) can be provided, which ensures the displacement of a metal bar to press it directly against the door 2A of the carrier 2, helping the contact between the two magnetic effect engagement members 21, 22.

The system is also set up with sensors to detect the closed condition and the open condition of the doors 2A, 5. With reference to FIG. 12, the closed condition is detected by engaging a pin 24 carried by the door 5 able to cooperate with a micro-switch 25 carried by the structure 4 of the station. The completely open condition of the door is detected by a proximity sensor 26 (also visible in FIG. 12) carried by the structure 4 and able to cooperate with a corresponding element of the door 5 (not visible in the drawings).

Returning to FIG. 3, the terminal end 1 of the pneumatic transport tube 1, being preferably inserted within the tubular structure 4 of station 3 for the entire axial extension of the station 3 (see also FIG. 2), has a window 1A at the door 5 of the structure of the station, to allow access to the carrier 2. Still with reference to FIG. 3, the terminal end 1 of the pneumatic transport tube has two windows 1B in diametrically opposite positions, at the area in which the flaps 8 for braking the carrier 2 are arranged.

One of the most critical moments in the movement of carrier 2 is just that related to reaching the end-stroke position in the arrival station. In a configuration in which the end portion of the pneumatic transport tube 1 would be end-connected to the tubular structure of the station, depressions would be created during operation which would make difficult the final movement of the carrier 2. This problem has been solved, in the system according to the invention, rightly by ensuring that the end portion of the transport tube 1 preferably fully enters into the tubular structure 4 of the station, obtaining the windows 1A and 1B, or by filling the eventual distance between the end portion of the tube 1 and the tubular structure 4 through the use of the above described bushing with telescopic gasket.

In the illustrated example, the door 5 of the station has its hinge axis which is placed, looking at the door from the front, on the right, but obviously an inverted orientation of the tubular structure 4 can be provided, so that the hinge axis would be on the left. Naturally, the carrier 2 can be inserted within the tube 1 with its ends oriented in one or in the opposite direction, since in any case the rotation to which it is subjected when it reaches the station ensures that it has too the hinge axis of its door on the appropriate side, corresponding to the positioning of the hinge axis of the door of the station.

With reference again to FIG. 12, the space inside the carrier 2 can be equipped with racks, shelves or the like configured to keep any type of support or container of histological samples in a stable position. FIG. 12 shows the example of a carrier 2 internally equipped with shelves on which cassettes C for the transport of histological samples are placed.

Figure 12A:
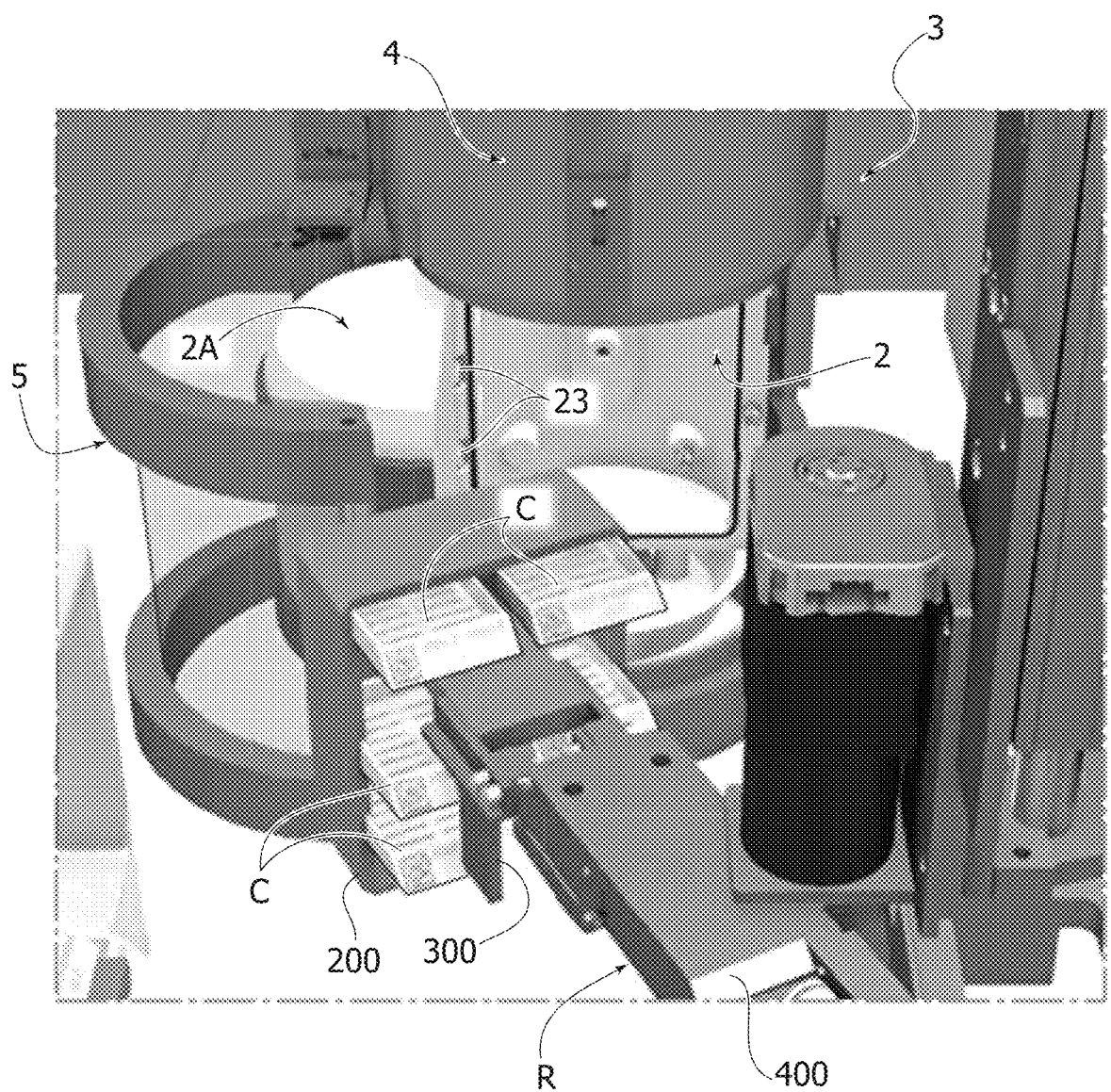
FIG. 12A is a perspective view showing a manipulator robot that picks up histological samples from a carrier that has been received in the station.

FIG. 12A shows the end part of an arm 400 of a manipulator robot R of any known type, arranged adjacent to the station 3, to carry out in a completely automated way the pick up operation of cassettes C from the carrier 2 after this has been open and/or the operation of loading cassettes C within the carrier 2. The manipulator robot R of the illustrated example is equipped with a gripper 300 which is able to extract from and reposition in the carrier an entire shelf structure 200 (clearly illustrated even in FIG. 7A) configured to support cassettes C.

Figure 13:
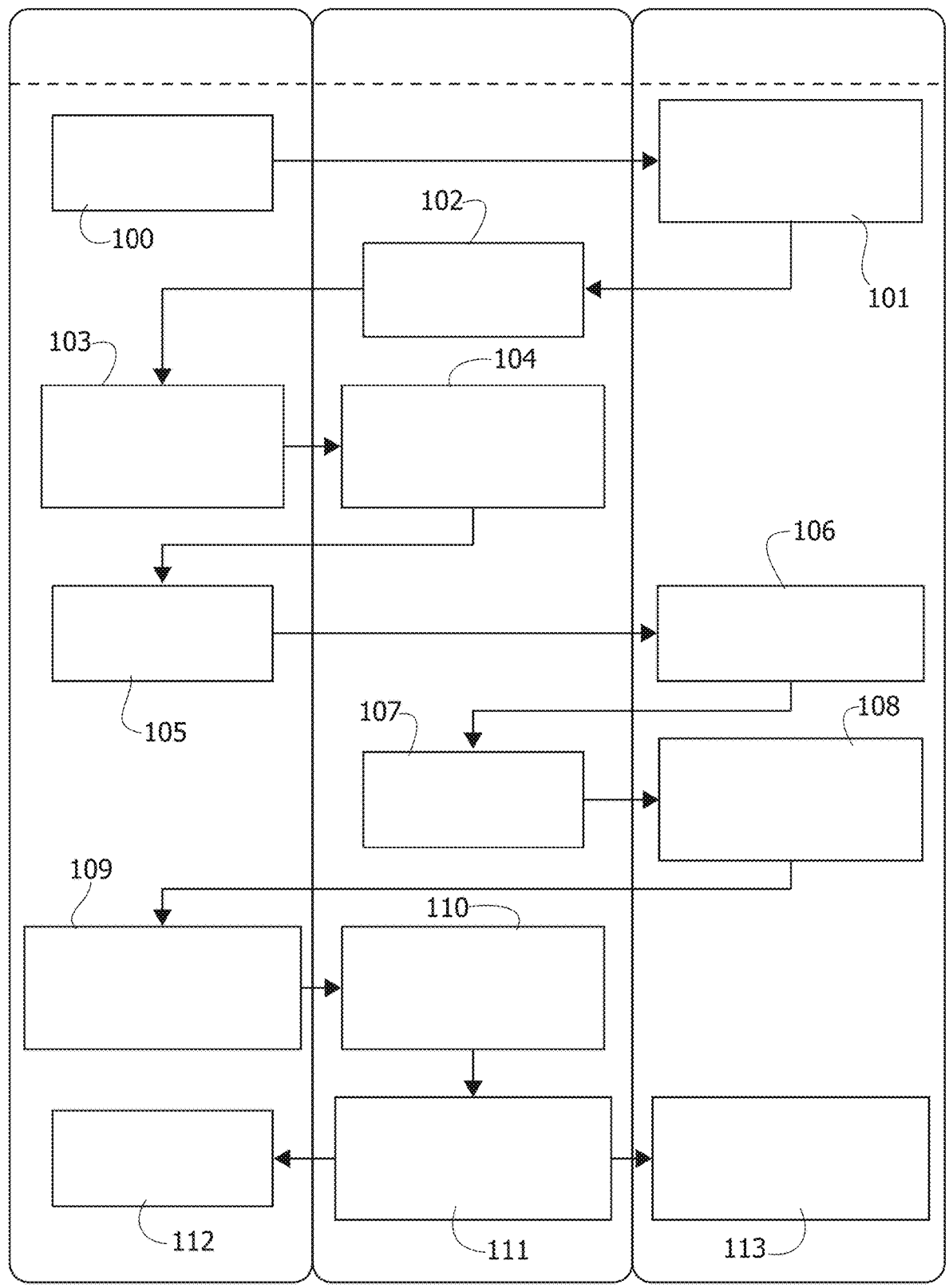
FIGS. 13, 14 are flow diagrams which illustrate an embodiment of the process according to the invention.

The operating flow of the preferred embodiment of the system according to the invention is illustrated in the flow diagram of FIG. 13, with reference to the step of arrival of a carrier at the station.

When a carrier arrives at the station (block 100), a sensor (for instance a photocell) signals the passage of the carrier to the electronic controller E (block 101). After this signaling, the blower in the pneumatic transport system is deactivated (block 102). When the carrier reaches the input of the station (block 103), the braking system 7 intervenes by further slowing the carrier down (block 104). Thus slowed down, the carrier finally reaches the end position within the station 3 (block 105) and this condition is detected by a sensor, for example a photocell (block 106). When such sensor signals the presence of the carrier in the station, the electronic controller activates the electric motor 14 which causes a rotation of the carrier about its axis (block 107). This rotation continues until a sensor detects that the position in which the door of the carrier is at the door of the station has been reached (block 108). In the aforementioned mating condition (block 109) it is activated the electric locking device to lock the carrier in position (block 110) after which the electrically operated lock for locking the door of the station is deactivated and a motor activates the opening of the door of the station, which in turn engages the door of the carrier (block 111). The opening of the door of the carrier is thus obtained (block 112) and the open condition of the doors is notified to the electronic controller (block 113), which can consequently activate the operating cycle of the manipulator robot.

Figure 14:
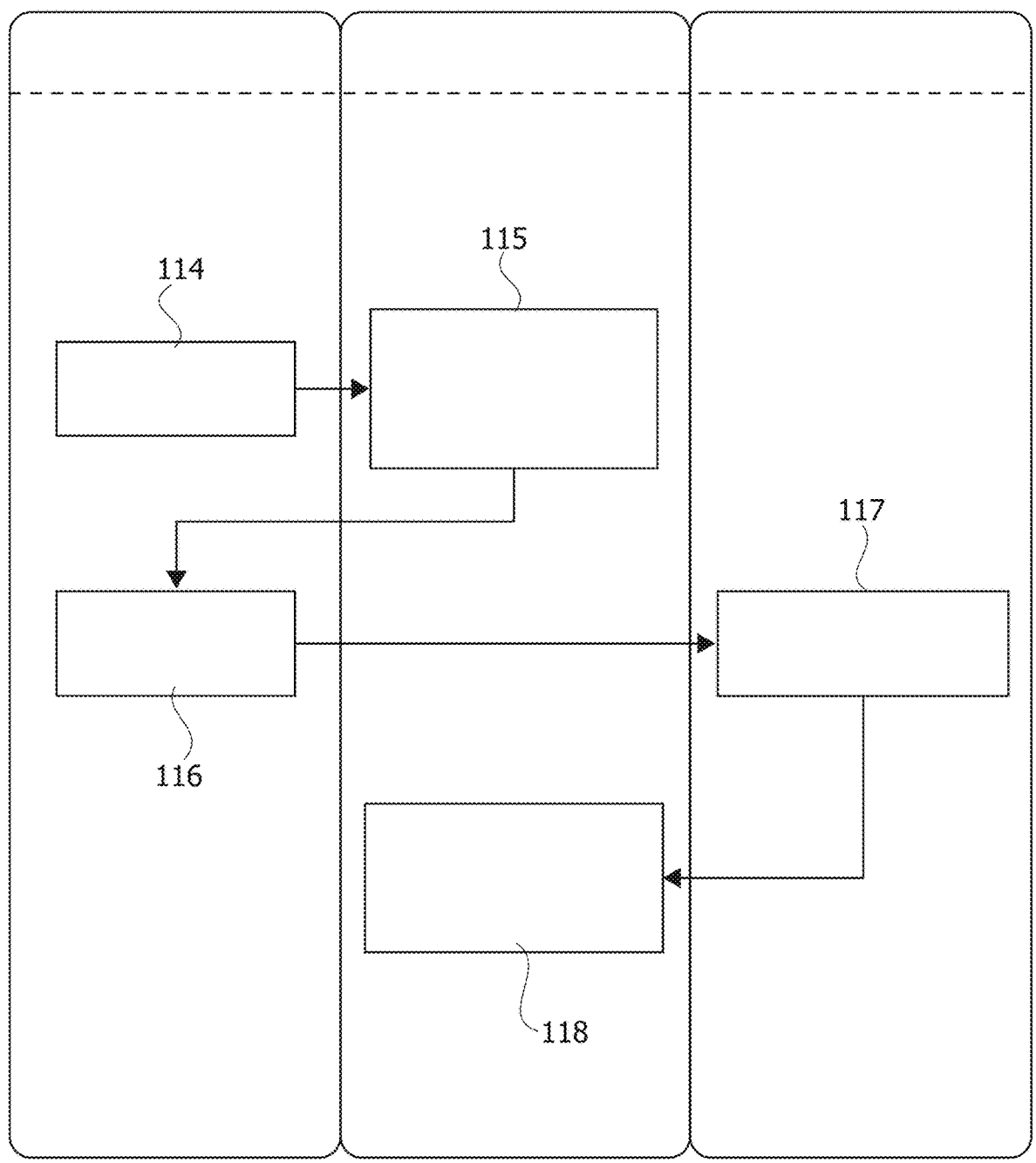

FIG. 14 shows the operating cycle corresponding to the departure of the carrier from the station, at the end of the operations carried out by the manipulator robot on the histological samples contained in the carrier. When the carrier is ready to restart (block 114) the door of the station is closed by the drive motor of the door (block 115), which also causes the closure of the door of the carrier (block 116). The closure of the door of the station is detected by the corresponding sensor (block 117), after which the electronic controller can activate the blower of the pneumatic transport system to cause the exit of the carrier from the station.

Naturally, without prejudice to the principle of the invention, the construction details and the embodiments may vary widely with respect to what is described and illustrated purely by way of example, without thereby departing from the scope of the present invention, as defined in the attached claims.

What is claimed is:

1. A pneumatic transport system for histological samples, comprising:
a pneumatic transport tube,
at least one carrier configured to be pneumatically transported in the pneumatic transport tube and arranged to contain histological samples, and
a station connected to said pneumatic transport tube, for loading and/or unloading the histological samples, wherein:
said carrier is in the form of a substantially cylindrical capsule, having a side carrier door with a hinge axis parallel to an axis of the carrier, said carrier door is configured to be moved between a closed position, for the transport of the histological samples through the pneumatic transport tube, and an open position, for the loading and/or unloading of the histological samples in/from the station,
said station comprises a station tubular structure coaxially connected to said pneumatic transport tube and arranged to receive the carrier at an end of a stroke of the carrier within the pneumatic transport tube, said station tubular structure having a station door in a side wall thereof, with a hinge axis parallel to an axis of the pneumatic transport tube, said station door is configured to be moved between a closed position and an open position,
said station further comprises a stop member, to stop said carrier when the carrier reaches a final position within the station, and a servo-controlled electric motor, to impart a rotation to said carrier around the axis of the carrier, by means of said stop member, until a mating condition is reached in which the carrier door is at an angular position substantially corresponding to an angular position of the station door,
said station further comprises an actuator to control a rotation of the station door between the station door closed position and the station door open position,
said station door and said carrier door are configured so as to engage each other when the carrier door is in said mating condition and said actuator controls an opening of the station door, so that an opening of the station door also causes an opening of the carrier door,
said system comprising an electronic controller configured to:
activate said servo-controlled electric motor which controls the rotation of the carrier about the axis of the carrier after the electronic controller has received a signal from a sensor which detects an arrival of the carrier at the final position in the station,
stop said servo-controlled electric motor, so as to stop said rotation of the carrier about the axis of the carrier and activate said actuator which controls the opening of the carrier door and of the station door, when the electronic controller receives a second signal from a second sensor which detects that said mating condition of the carrier door and the station door has been reached,
so that when said carrier reaches said station, accessibility to the histological samples contained in the carrier is obtained in an automated manner.

2. The system according to claim 1, further comprising a manipulator robot for the automatic loading and/or unloading of histological samples into/from the carrier, said electronic controller being configured to enable a cycle of operations of said manipulator robot after the electronic controller has received the second signal from said second sensor which detects said mating condition of the carrier door and of the station door, and/or a third signal from a third sensor which detects the open condition of the station door and/or the open condition of the carrier door.

3. The system according to claim 2, wherein a fourth sensor, located in a position spaced from said station, and configured to detect the passage of the carrier arriving at the station, is associated with said pneumatic transport tube and wherein the electronic controller is configured to deactivate a blower of the pneumatic transport system when the electronic controller receives from said fourth sensor a fourth signal indicating the passage of the carrier arriving at the station.

4. The system according to claim 1, wherein said station tubular structure is provided with an electrically operated locking device, to lock the carrier in said mating condition of said carrier door and said station door and wherein said electronic controller is configured to activate said locking device after the electronic controller has stopped said rotation of the carrier and before the electronic controller controls the opening of the station door and the carrier door.

5. The system according to claim 1, wherein said pneumatic transport tube is provided, adjacent to said station tubular structure, with a braking device to brake movement of the carrier and comprising one or more elastically biased flaps, protruding inside the pneumatic transport tube and configured so that the flaps engage the carrier when the carrier is close to reaching the station, so as to slow the carrier down, while the flaps do not substantially oppose the movement of the carrier when the carrier leaves again from the station and moves in an opposite direction in the pneumatic transport tube.

6. The system according to claim 1, wherein said stop member able to impart the rotation to the carrier about the axis of the carrier is rotatably mounted at one end of said station tubular structure and is provided with shock-absorbing pads configured to be engaged by a front wall of the carrier when it reaches the final position within the station at the end of the stroke in the pneumatic transport tube.

7. The system according to claim 1, wherein said station is provided with sensors to detect a closed condition of the station door and/or of the carrier door and to detect an open condition of the station door and/or of the carrier door.

8. The system according to claim 1, wherein the carrier door is biased towards the open position by one or more springs.

9. The system according to claim 1, wherein a wall of the carrier and the carrier door are provided with respective magnetic engagement members tending to hold the carrier door in the closed condition.

10. The system according to claim 1, wherein the station door is provided with an electrically operated lock for locking the station door in the station door closed position, said electronic controller being configured to deactivate said electric lock before controlling an opening of the station door.

11. The system according to claim 1, wherein the pneumatic transport tube comprises an end portion inserted within said station tubular structure through an entire axial extension of said station tubular structure, said end portion of the pneumatic transport tube having a window at the station door.

12. The system according to claim 1, wherein the carrier is internally configured to hold one or more supports of histological samples in a stable position.

13. The system according to claim 1, wherein the pneumatic transport tube and the station tubular structure are oriented with their axis directed vertically, and with the station tubular structure associated with a lower end of the pneumatic transport tube.

14. A process for transporting and handling histological samples, wherein a pneumatic transport system for histological samples is provided, said system comprising:
a pneumatic transport tube,
at least one carrier configured to be pneumatically transported in the pneumatic transport tube and arranged to contain histological samples, and
a station connected to said pneumatic transport tube, for loading and/or unloading the histological samples,
wherein:
said carrier is in the form of a substantially cylindrical capsule, having a side carrier door with a hinge axis parallel to an axis of the carrier, said carrier door is configured to be moved between a closed position, for the transport of the histological samples through the pneumatic transport tube, and an open position, for the loading and/or unloading of the histological samples in/from the station,
said station comprises a station tubular structure coaxially connected to said pneumatic transport tube and arranged to receive the carrier at an end of a stroke of the carrier within the pneumatic transport tube, said station tubular structure having a station door in a side wall thereof, with a hinge axis parallel to the axis of the pneumatic transport tube, said station door is configured be moved between a closed position and an open position,
said station door and said carrier door are configured so as to engage each other when the carrier door is at an angular position substantially corresponding to an angular position of the station door, so that in this condition, an opening of the station door also causes an opening of the carrier,
said process comprising the following operations:
detecting, by means of a sensor, when the carrier reaches a final position against a stop member within said station tubular structure at the end of the stroke of the carrier within the pneumatic transport tube,
activating, by means of an electronic controller, a servo-controlled electric motor which imparts a rotation to said carrier about the axis of the carrier, by means of said stop member, after the electronic controller has received the signal from said sensor which detects an arrival of the carrier at the final position in the station,
stopping, by means of the electronic controller, said servo-controlled electric motor and consequently stopping the rotation of the carrier, when the electronic controller receives a second signal from a second sensor which detects a reaching of a mating condition in which the carrier door is at an angular position substantially corresponding to the angular position of the station door,
activating, by means of said electronic controller, an actuator which controls an opening of the station door and consequently an opening of the carrier door after that the carrier has been stopped in said mating condition of the station door and the carrier door,
so that when the carrier is in said station, accessibility to the histological samples contained in the carrier is obtained in an automated manner.

15. The process according to claim 14, further comprising enabling, by means of said electronic controller a cycle of operations of a manipulator robot configured to perform loading and/or unloading operations of histological samples into/from the carrier, after the electronic controller has received the second signal from said second sensor which detects said mating condition of the carrier door and the station door, and/or a third signal from a third sensor which detects the open condition of the station door and/or the open condition of the carrier door.

16. The process according to claim 15, further comprising deactivating, by means of said electronic controller, a blower of the pneumatic transport system, after the electronic controller has received a fourth signal from a fourth sensor indicating a passage of the carrier arriving at the station.

17. The process according to claim 14, further comprising activating, through said electronic controller, an electrically operated locking device, to lock the carrier in said mating condition of said carrier door and said station door after the electronic controller has stopped the rotation of the carrier and before the electronic controller controls the opening of the station door and the carrier door.

18. The process according to claim 17, further comprising controlling, by means of said electronic controller, when the manipulator robot has completed the cycle of loading and/or unloading operations of histological samples into/from the carrier, a closure of the station door, with a consequent closure of the carrier door, a deactivation of said locking device and an activation of a blower of the pneumatic transport system, to transport the carrier out and away from the station.

19. The process according to claim 14, further comprising braking movement of the carrier arriving at the station by means of a braking device comprising one or more elastically biased flaps, protruding inside the pneumatic transport tube, said flaps being configured so that the flaps engage the carrier when the carrier is close to reaching the station, so as to slow the carrier down, and so that the flaps do not substantially oppose the movement of the carrier when the carrier leaves again from the station and moves in an opposite direction in the pneumatic transport tube.

20. The process according to claim 14, further comprising deactivating, by means of said electronic controller, an electric lock which locks the station door in the station door closed position, before controlling an opening of the station door and activating, by means of said electronic controller, said electric lock after a closure of the door of the station has been controlled.

* * * * *